United States Patent
Legay et al.

(10) Patent No.: US 6,187,547 B1
(45) Date of Patent: Feb. 13, 2001

(54) ASSAY KIT

(75) Inventors: François Legay, Huningue (FR); Roland Wenger, Riehen (CH)

(73) Assignee: Novartis AG, Basel (CH)

( * ) Notice: Under 35 U.S.C. 154(b), the term of this patent shall be extended for 0 days.

(21) Appl. No.: 09/131,042

(22) Filed: Aug. 6, 1998

Related U.S. Application Data

(63) Continuation of application No. 08/637,683, filed on Mar. 7, 1996, now abandoned.

(30) Foreign Application Priority Data

Sep. 8, 1993 (GB) .................................................. 9318612

(51) Int. Cl.[7] .............................. A61K 38/12; C07K 1/00; C12Q 1/00; G01N 33/53; G01N 33/566
(52) U.S. Cl. ................................ 435/7.1; 435/4; 435/7.9; 436/501; 436/536; 514/885; 530/317; 530/321; 530/350
(58) Field of Search ..................................... 436/501, 536; 530/317, 321, 350; 435/4, 7.1, 7.9; 514/885

(56) References Cited

U.S. PATENT DOCUMENTS 5,427,960  6/1995  Wang et al. ........................ 436/536

FOREIGN PATENT DOCUMENTS

| | | |
|---|---|---|
| 0293892 | 7/1988 | (EP) . |
| 0296122 | 12/1988 | (EP) . |
| 296123 | 12/1988 | (EP) . |
| 9218527 | 10/1992 | (WO) . |

OTHER PUBLICATIONS

M.D. Walkinshaw, et al., Transplantation Proceedings, vol. 24, No. 4/2, pp. 8–13 (Aug. 1992).

Lawen et al., Journal of Biological Chem. 266 (24): 15567–15570, (1991).

*Primary Examiner*—James C. Housel
*Assistant Examiner*—V. Ryan
(74) *Attorney, Agent, or Firm*—Diane E. Furman

(57) ABSTRACT

A new method of measuring blood levels of immunophilin-binding pharmaceuticals, e.g., cyclosporins, rapamycins, and FK506 compounds is provided, comprising the novel step of displacing the pharmaceutical from its immunophilin by using a binding competitor, thereby eliminating the need for an extraction step and enhancing the simplicity and accuracy of the assay. Assay kits comprising a binding competitor and a receptor, e.g., a monoclonal antibody, which binds to the pharmaceutical but not significantly to the binding competitor are also provided, as are new uses of immunophilin-binding compounds as binding competitors in such assays.

20 Claims, No Drawings

ASSAY KIT

This application is a continuation of Application No. 08/637,683 filed Mar. 7, 1996, abandoned.

This invention relates to an assay procedure and kit for use in determining the levels of drug substances in unextracted blood in the presence of specific binding proteins. The assay is particularly suitable for determining the blood levels of immunophilin-binding drugs, e.g., cyclosporins, rapamycins, or FK506 compounds.

Cyclosporins comprise a class of structurally distinct, cyclic, poly-N-methylated undecapeptides, generally possessing immunosuppressive, anti-inflammatory, anti-viral and/or anti-parasitic activity, each to a greater or lesser degree. The first of the cyclosporins to be identified was the fungal metabolite Cyclosporin A, or Ciclosporin, and its structure is given in The Merck Index, 11th Edition; Merck & Co., Inc.; Rahway, New Jersey, USA (1989) under listing 2759. Later cyclosporins to be identified are cyclosporins B, C, D and G which are also listed in the Merck Index under listing 2759. A large number of synthetic analogues are also known and representative examples are disclosed in EP 296 122, EP 484 281, and GB 2222770.

Rapamycin is a macrolide immunosuppressant that is produced by *Streptomyces hygroscopicus* and which has been found to be pharmaceutically useful in a variety of applications, particularly as an immunosuppressant for use in the treatment and prevention of organ transplant rejection and autoimmune diseases. The structure of rapainycin is given in Kesseler, H., et al.; 1993; *Helv. Chim. Acta*; 76: 117. Large numbers of derivatives of rapamycin have been synthesized, including for example certain acyl and aminoacyl-rapamycins (e.g., U.S. Pat. No. 4,316,885, U.S. Pat. No. 4,650,803, and U.S. Pat. No. 5,151,413), 27-desmethyl-rapamycin (WO 92/14737), 26-dihydro-rapamycin (U.S. Pat. No. 5,138,051), certain pyrazole derivatives (U.S. Pat. No. 5,164,399), certain alkoxyester derivatives (U.S. Pat. No. 5,233,036), and 40-O-alkylated derivatives (WO 94/09010). Rapamycin and its structurally similar analogues and derivatives are termed collectively as "rapamycins" in this specification.

FK506 is a macrolide immunosuppressant that is produced by *Streptomvces tsukubaensis* No 9993. The structure of FK506 is given in the appendix to the Merck Index, as item A5. Also a large number of related compounds which retrain the basic structure and immunological properties of FK506 are also known. These compounds are described in a large number of publications, for example EP 184162, EP 315973, EP 323042, EP 423714, EP 427680, EP 465426, EP 474126, WO 91/13889, WO 91/19495, EP 484936, EP 532088, EP 532089, WO 93/5059 and the like. These compounds are termed collectively "FK506 compounds" in this specification.

Due to their extremely useful pharmaceutical properties, cyclosporins (and Cyclosporins A and G in particular), rapamycins and FK506 compounds have wide application in, for example the prevention of transplant rejection and in the treatment of auto-immune diseases. However these compounds have side effects at higher doses and therefore their concentration in the blood must be kept within certain therapeutic ranges. Bioavailabilities and metabolic conversion rates tend to be patient specific and hence dosaging is patient specific. It is therefore necessary to monitor the concentration of these immunosuppressants in the blood at regular intervals.

Certain assay procedures based upon high pressure liquid chromatography (HPLC) have been developed but are either cumbersome to use or are not specific enough. For cyclosporin A and FK-506, specific monoclonal antibodies have been developed and assay procedures based on the antibodies provided. However all the assay procedures provided to date require the blood or plasma sample to be first extracted with a solvent (such as methanol) which is then removed by evaporation or dilution. The antibody is then added to the sample and a radioimmunoassay (RIA) analysis performed. The assay procedure based on the specific monoclonal antibody works well but the need for the extraction step and the subsequent removal of the solvent can result in the assay becoming less sensitive and less precise if care is not taken. Therefore the assay must be carried out by skilled technicians and is a time consuming procedure.

Hence, given the importance of cyclosporins, rapamycins and FK506 compounds as pharmaceuticals, there is a need for simple, sensitive assays to determine their concentrations in blood.

Accordingly this invention provides an assay procedure for determining the concentration of a immunophilin-binding pharmaceutical in blood; the procedure comprising adding a binding competitor that displaces the pharmaceutical from immunosuppressant-immunophilin complexes in the blood; adding a receptor that binds to the pharmaceutical but not significantly to the binding competitor, separating the receptor-pharmaceutical complex from the sample; and determining the amount of the pharmaceutical.

It has been found that a portion of a cyclosporin, rapamycin or FK506 compound present in blood exists in the form of a pharmaceutical-immunophilin complex. If the pharmaceutical is displaced from the complex using a binding competitor, it is then not necessary to extract the blood sample using methanol and hence the disadvantages associated with methanol extraction and removal are removed. The resultant assay procedure gives accurate results, is simple and is a surprising break-through in the assaying of cyclosporins, rapamycins or FK506 compounds. For example, the assay procedure is able to detect concentrations as low as 0.7 ng (cyclosporin A)/ml (of whole blood) with a coefficient of variation of less than 30%. This is much better than the cyclosporin A assay that is commercially available.

Immunophilins are a family of intracellular binding proteins which bind cyclosporins, rapamycins or FK506 compounds. Two distinct families of immunophilins are presently known; cyclophilins which bind to cyclosporins, and macrophilins which bind to rapamycins and FK506 compounds. The structures of certain immunophilins are described in Walkinshaw et al; 1992; *Transplantation Proceedings*, 24, 4(2), 8–13. Specific examples are cyclophilin A and macrophilin-12 (often known as FKBP-12).

The amount of the binding competitor to be used to displace the pharmaceutical from the immunophilin-pharmaceutical complex is likely to vary from pharmaceutical to pharmaceutical and from binding competitor to binding competitor. However, in each case, an optimum range may be readily determined carrying out the assay procedure at several concentrations (including a blank) of the pharmaceutical and at several concentrations of the binding competitor. The samples are then diluted two or three times and the procedures carried out again on each dilution. The sensitivities of the tests are then compared and those concentrations of binding competitor that give decreased sensitivity are discarded.

The receptor which binds to the pharmaceutical may be any specific binding compound as is used in conventional assays, e.g., polyclonal, monoclonal, or recombinant antibodies, antibody fragments, or molecular imprinted polymers (e.g., as described by Vlatakis, et al., (1993) Nature, 361:645), preferably a monoclonal antibody.

Once the pharmaceutical is released from the pharmaceutical-immunophilin complex, the amount of the pharmaceutical bound to the receptor may be determined using any assay method, preferably a monoclonal antibody based assay, e.g., a competitive assay measuring the ability of the pharmaceutical to compete for binding to the antibody or receptor, or a noncompetitive assay. A competitive assay preferably uses, e.g., a labeled pharmaceutical (tracer) as competitor for the antibody, in the presence and absence of the test sample. The tracer may be labeled with a label capable of providing a suitable readout, e.g., radioactive, fluorescent, luminescent or colorimetric readout as is conventional in the art. Alternatively, the competitor for the receptor may be unlabeled pharmaceutical (optionally the pharmaceutical-protein immunogenic conjugate used to raise the antibody) coated onto the surface of the test chamber, e.g., in an enzyme-linked immunosorbent assay (ELISA) or in a system where the antibody for the pharmaceutical is itself labeled. The antibody or receptor may be free in the test solution or coated onto the wall of the test chamber, depending on the assay system used. In a competitive assay, the readout (e.g., amount of tracer bound to antibody or receptor) is inversely proportional to the amount of pharmaceutical in the test sample. Standard solutions containing known concentrations of the pharmaceutical may be used to standardize the assay as is conventional.

When we refer to a receptor that binds to the pharmaceutical but not significantly to the binding competitor, we mean that the extent of receptor cross reactivity between pharmaceutical and binding competitor is not sufficient to significantly affect the sensitivity of the assay. The precise amount of cross reactivity between the binding competitor and the pharmaceutical (and/or the binding competitor and the tracer in a competitive assay) which can be tolerated of course varies to some extent on the relative affinity of the binding competitor to the immunophilin compared to the pharmaceutical: the higher the affinity, lower the concentration needed to displace the pharmaceutical and the greater receptor cross reactivity that can therefore be tolerated without affecting the accuracy of the assay. In practice, the significance of cross reactivity is best measured by comparing standard curves using different amounts of binding competitor, once the minimum concentration of binding competitor for displacement of the pharmaceutical is reached, the standard curves should not vary significantly as the binding competitor concentration increased to the highest level contemplated for use in the assay, thereby demonstrating that any cross reactivity with the antibody is insignificant in the context of the assay (if there was cross reactivity with the antibody, the presence of high concentration of binding competitor would tend to inflate the observed measurement of drug levels because the assay would measure drug plus binding competitor). The significance of any variation between the standard curves in the presence and absence of binding competitor can be assessed using standard statistical methods, e.g., a t-test. As a guideline, however, because the binding competitor is usually present in much higher concentration than pharmaceutical in the test sample, the receptor cross reactivity between the pharmaceutical and the binding competitor should be, e.g., below 1%, preferably below 0.1%, as measured in a competitive assay in buffer.

In one aspect of the invention, the pharmaceutical is a cyclosporin and the binding competitor is a cyclosporin analog that binds to cyclophilin. Preferably the binding competitor is [$Thr^2$, $Leu^5$, $D-Hiv^8$, $Leu^{10}$]-Ciclosporin which is described in EP 296 122. and which competitively binds to cyclophilin A. Preferably the receptor is a cyclosporin specific, monoclonal antibody, e.g., as described in WO 8612080. Examples of cyclosporins are the immunosuppressants cyclosporin A and cyclosporin G, and the anti-HIV replication compound [$MeIle^4$]-Ciclosporin disclosed in EP 484 281.

Where a competitive assay is used to measure a cyclosporin, the competitor for the receptor may be a cyclosporin bound to the wall of the test chamber (e.g., a cyclosporin-protein conjugate as described in WO 86/2080), or a labeled cyclosporin (a tracer), e.g., (i) a radiolabeled cyclosporin, e.g., tritiated dihydrocyclosporin A, or (ii) a labeled derivative of [$Thr^2$]-Ciclosporin, [$(D)Lys^8$]-Ciclosporin, or [$O$-2-hydroxyethyl$(D)Ser^8$]-Ciclosporin, e.g., a derivative having a label which is capable of providing a fluorescent, luminescent or colorimetric signal, e.g., a dansyl or biotinyl derivative, e.g., [$\epsilon$-N-biotinyl$(D)Lys^8$]-Ciclosporin or [$O$-(2-biotinoyloxyethyl)$Thr^2$]-Ciclosporin. Such labeled cyclosporins are prepared generally as described in WO 86/2080, or by using one of the numerous kits for labeling compounds which are commercially available, for example, from Sigma or Amersham.

A particularly preferred method for measuring Ciclosporin levels comprises coating the wall of a test chamber (e.g., a microtiter plate) with Ciclosporin-specific monoclonal antibody (e.g., by coating the chamber with goat anti-mouse antibody, then allowing the Fc region of the Ciclosporin-specific monoclonal antibody to bind to the goat anti-mouse antibody so that the binding region of the Ciclosporin antibody is free). The sample to be tested (e.g., blood from a patient), the binding competitor (e.g., [$Thr^2$, $Leu^5$, $D-Hiv^8$, $Leu^{10}$]-Ciclosporin), and labeled (e.g., biotin labeled) cyclosporin tracer (e.g., [$O$-(2-biotinoyloxyethyl) $Thr^2$]-Ciclosporin) are then combined together in the test chamber and incubated for a fixed period. The period of incubation is a period sufficient to allow the antibody to bind with the pharmaceutical and the tracer, e.g., at least one hour, preferably at least two hours. The test chamber is then rinsed. The level of bound tracer is measured by conventional means depending on the type of label used; a biotin label may be recognized, for example, using a commercial assay with streptavidin (a bacterial protein with a high affinity to biotin) linked to an enzyme, e.g., horseradish peroxidase, which cleaves a substrate to give a fluorescent, luminescent or colorimetric readout.

In another aspect of the invention, the pharmaceutical is an FK506 compound, e.g., FK506, and the binding competitor is a compound that binds to macrophilin 12. Any suitable macrophilin 12 binding compound that is able to displace the FK506 compound may be used. Rapamycin competes with FK506 for binding to macrophilin-12, and is preferably used as the binding competitor. Suitable FK506 compound antibodies may be used for detection; preferably specific antibodies, e.g., as described in EP-A 0 293 892. Where a competitive assay is used, the competitor for the antibody may be an FK506 compound bound to the assay plate or preferably a labeled derivative of FK506, e.g., a radiolabeled derivative, e.g., tritiated FK506, or other labeled derivative, e.g., POD-FK506 (described as POD-labeled FR-900506 in EP-A 0293 892).

In a third aspect of the invention, the pharmaceutical is a rapamycin, e.g., Rapamycin or the 40-O-hydroxyethyl-rapamycin of WO 94/09010, and the binding competitor is a compound that binds to macrophilin 12. Any suitable macrophilin 12 binding compound that is able to displace the rapamycin may be used. FK506 competes with Rapamycin for binding to macrophilin-12, and is preferably used as the binding competitor. The receptor is preferably a rapamycin-specific monoclonal antibody. [Note: Monoclonal antibody selective for a rapamycin has not been described in the literature. We have prepared highly selective antibody, however, using standard Köhler-Milstein techniques wherein the antigen is an immunogenic conjugate of rapamycin, e.g., a rapamycin linked to an immunogenic protein through one of the hydroxy groups on the rapamycin, preferably the hydroxy group located on the cyclohexyl portion of the rapamycin (position 40 of Rapamycin) or the hydroxy corresponding to position 28 on Rapamycin. The rapamycin is linked to the protein by first making a rapamycin bearing an activated coupling group and then coupling the activated rapamycin to the protein. The activated coupling group is a group capable of direct reaction with a protein to form a covalent linkage without the requirement for the use of a coupling agent (e.g., carbodiimide reagents) to enable, effect, or promote the reaction with the protein). For example, 40-O-activated rapamycin is O-acylated using succinic anhydride in the presence of DMAP and pyridine to form the rapamycin hemisuccinate (40-O-(3-Carboxy)propanoyl-rapamycin); which is then activated with N-hydroxy succinimide in the presence of EDC, $Et_3N$, and $CH_2Cl_2$ to form the succinimidooxysuccinyl rapamycin (40-O-(3-Carboxy)propanoyl-rapamycin N-hydroxysuccinimide ester). 28-O-activated rapamycin is prepared analogously using prior protection at the 40-hydroxy, then linked to the protein to prepare 28-O-linked immunogenic conjugate which can be used to prepare antibody having different specificity from that obtained using 40-O-linked conjugate, e.g., highly sensitive to differences in the cyclohexyl region of the rapamycin.] Where a competitive assay is used, the competitor for the antibody may be a rapamycin bound to the assay plate, or preferably a labeled rapamycin, e.g., a fluorolabeled rapamycin, prepared, e.g., by reacting an activated rapamycin as described above with a labeling group, e.g., biotin or dansyl, or by radiolabeling the rapamycin, e.g., tritiating the rapamycin.

The assay procedure of the invention has the advantages that it may be carried out rapidly and simply using standard bioanalytical equipment to give accurate and reproducible results. Also, whole blood may be used without the need for extraction.

The invention also provides an assay kit suitable for detecting the amount of an immunophilin-binding pharmaceutical in blood the kit comprising a binding competitor that displaces the pharmaceutical from pharmaceutical-immunophilin complexes in the blood; and an antibody that binds to the pharmaceutical but not significantly to the binding competitor.

Preferably the antibody is a monoclonal antibody that is specific to the pharmaceutical.

If the pharmaceutical is a cyclosporin, the binding competitor may be a cyclosporin analog that binds to cyclophilin. Preferably the binding competitor is [$Thr^2$, $Leu^5$, $D-Hiv^8$, $Leu^{10}$]-Ciclosporin. Preferably the antibody is a Ciclosporin-specific monoclonal antibody as described in WO 86/2080.

If the pharmaceutical is a FK506 compound or a rapamycin, the binding competitor may be rapamycin or FK506, respectively, or an analog thereof that binds to macrophilin 12. Any suitable antibody to a FK506 compound or rapamycin compound may be used; preferably specific antibodies, e.g., prepared as described above for rapamycin or as described in EP-A 0 293 892.

The kit may further comprise an appropriately labeled tracer, standard and instructions for use. The label for the tracer may be any suitable label, e.g., a radioactive, fluorescent or calorimetric label. Where convenient, the components of the kit may be in lyophilized form.

Finally, in a further embodiment, the invention provides a new use for an immunophilin-binding compound as an immunophilin-binding competitor in an assay kit or procedure to measure blood levels of another immunophilin-binding compound; e.g., the use of [$Thr^2$, $Leu^5$, $D-Hiv^8$, $Leu^{10}$]-Ciclosporin in an assay kit or procedure to measure blood levels of a cyclosporin; the use of Rapamycin in an assay kit or procedure to measure blood levels of an FK506 compound; and the use of FK506 in an assay kit or procedure to measure blood levels of a rapamycin.

Examples of the invention are now described, by way of example and not limitation. It will be apparent to one skilled in the art that variations in the precise concentrations of reagents and reaction conditions may be tolerated, so long as the variations are consistent from assay to assay. Other assay systems using binding competitor to release a pharmaceutical from an immunophilin-pharmaceutical complex are considered within the scope of the invention; once the pharmaceutical is freed from the immunophilin-pharmaceutical binding complex, it may of course be measured in any conventional way.

EXAMPLE 1

Cyclosporin A Assay

Calibration samples: 16 µg of Cyclosporin A are added to 1 ml of 70% v/v aqueous ethanol and stored at 4° C. 50 µl of the Cyclosporin A solution are diluted in 1 ml of human blood (obtained from the Blutspendezentrum Basel) to give a Cyclosporin A concentration of 800 ng/ml. Calibration samples of concentrations 400 ng/ml, 200 ng/ml, 100 ng/ml, 50 ng(ml, 25 ng/ml, 12.5 ng/ml, 6.2 ng/ml, 3.1 ng/ml, 1.6 ng/ml 0.8 ng/ml and 0.4 ng/ml are then prepared by successively diluting 500 µl of the Cyclosporin A solution in 1 ml human blood. A blood sample without Cyclosporin A is prepared as a blank.

Conditioned Microtiter Plates: Each well of several 96 well microtiter plates is coated with 100 µl of goat anti-mouse antibody (GaM IgG Fc unconjugated, Pierce 31170) diluted to 10 µg/ml in phosphate buffer saline (PBS). The microtiter plates are incubated overnight at 4° C. The goat anti-mouse antibody is discarded and 200 µl of a blocking solution (2 g of Bovine Serum Albumin dissolved in 100 ml PBS) is added to each well. The microtiter plates are incubated at 37° C. for two hours and then washed on a plate washer using 3×300 µl of a PBS/Tween 20 solution (0.5 g Tween 20 in 1 liter PBS). The conditioned microtiter plates are stored at 4° C.

Antibody Plate: 1 ml of PBS/Tween 20 solution is added to a vial of cyclosporin A specific, monoclonal antibody in lyophilized form. The antibody is described in WO 86/2080 and forms part of the commercially available Sandimmun®-kit. The antibody solution is then diluted 1:10 with PBS/Tween 20 solution and 100 µl are pipetted to selected wells of a conditioned microtiter plate. 100 µl of PBS/Tween 20 solution are pipetted to the remaining wells. The microtiter plate is incubated overnight at 4° C.

Cyclosporin Tracer: A vial containing 1 ml of radioactive dihydrogenated Cyclosporin A in 96% v/v aqueous ethanol is obtained from the commercially available Sandimmun®-kit.

Competitor Solution: 4.2 mg of [Thr$^2$, Leu$^5$, D-Hiv$^8$, Leu$^{10}$]-Ciclosporin, produced as described in EP 296 122, are dissolved in 1 ml methanol and stored at 4° C.

125 μl of each calibration sample (including the blank) are pipetted into well of an unconditioned microtiter plate. 125 μl of the blood samples to be tested are pipetted in each of the remaining wells. 100 μl of PBS/Tween 20 solution and 25 μl of cyclosporin tracer are added to each well. The microtiter plate is shaken for 5 minutes and then incubated at room temperature for 15 minutes. 3 μl of competitor solution are added to each well, the microtiter plate shaken for 5 minutes and the treated calibration samples and treated blood samples incubated overnight at 4° C.

An antibody plate is washed 3× with 300 μl of PBS/Tween 20 solution and 100 μl of treated calibration sample or treated blood sample are added to each well. The microtiter plate is incubated for 3 hours at 4° C. and then washed 3× in 300 μl PBS/Tween 20 solution. 100 μl of 1 g sodium dodecylsulphate dissolved in 100 ml water are added to each well, the microtiter plate shaken for 5 minutes at room temperature and then incubated for 15 minutes at 37° C. 100 μl of solution from each well are then analyzed using a Packard 2000CA liquid scintillation analyzer.

A calibration curve is prepared from the results obtained from the calibration samples. The curve is represented as percentage of antibody-tracer binding compared to blank plotted against the log of Cyclosporin A concentration.

The coefficient of variation for the results is less than 30% over the range 0.7 ng Cyclosporin A/ml blood to 400 ng Cyclosporin A/ml blood. This working range indicates that high accuracy may be obtained even at very low concentrations.

The consistency of the assay is confirmed by repetition. 100 ng and 400 ng of Cyclosporin A are each reconstituted in 1 ml human blood to obtain concentrations of 100 ng/ml and 400 ng/ml. Each sample is analyzed four times using the procedure described in example 1 to determine the concentration. The results are set out in table 1

TABLE 1

| Test | Control (ng/ml) | Mean Measured Value (ng/ml) | % Deviation |
|---|---|---|---|
| 1 | 100 | 99.0 | 1 |
|   | 400 | 450.0 | 12.5 |
| 2 | 100 | 102.0 | 2 |
|   | 400 | 405.5 | 1.4 |
| 3 | 100 | 99.5 | 0.5 |
|   | 400 | 429.5 | 7.4 |
| 4 | 100 | 90.0 | 10 |
|   | 400 | 385.5 | 3.6 |

For 100 ng/ml, the overall mean is 97.6 ng/ml giving an average deviation of 2.4% For 400 ng/ml, the overall mean is 417.6 ng/ml giving an average deviation of 4.4%.

The results indicate that a high degree of accuracy is obtainable consistently.

EXAMPLE 2

FK06 Assay

Microtiter plate preparation: Each well is coated with 100 μg/ml goat anti-rabbit antibody in phosphate buffer saline (PBS). The microtiter plates are incubated overnight at 4° C. The goat anti-rabbit antibody is discarded and 200 μl of blocking solution (2 g of min dissolved in 100 ml of PBS) is added to each well. The microtiter plates are incubated 2 hours at 37° C. and then washed on a plate washer using 3× 300 μl of a PBS/Tween 20 solution (0.5 g of Tween 20 in 1 liter PBS). The microtiter plates are stored at 4° C.

One hundred μl of rabbit anti-FK506 antibody diluted 1000 times in PBS/Tween 20 solution are added in each well. The microtiter plate is incubated overnight at 4° C.

Calibration samples: FK506 is diluted either in human whole blood or in PBS/Tween 20 at 200 ng/ml, 20 ng/ml and 2ng/ml. A blood sample without FK 506 is prepared as a blank.

Competitor Solution: FK 506 labeled with tritium is diluted in order to have 10000 cpm in 25 μl.

Assay: 125 μl of calibration sample in whole blood or in buffer are added and mixed with 100 μl of PBS/Tween 20 containing 50, 10, 1 and 0 μg/ml of Rapamycin. 25 μl of competitor solution are added in each well. The microtiter plate is incubated 3 h at 4° C. and then washed 3 times with 300 μl of PBSTween 20. 100 μl of 1 g sodium dodecylsulfate dissolved in 100 ml water are added to each well, and the microtiter plate is shaken for 5 minutes and then 15 minutes at 37° C. 100 μl of solution from each well are then analyzed using a Packard 2000CA liquid scintillation analyzer.

Results: The assay using samples in buffer gives similar standard curves with the different concentration of rapamycin as displacement agent. This result shows that the rabbit anti-FK 506 antibody does not cross react with rapamycin.

The assay using samples in whole blood gives a very low signal when no Rapamycin is used as displacement agent because SK 506 is bound to the binding proteins contained in whole blood and is not available to react with the antibody. When Rapamycin is added as a binding competitor for macrophilin, the standard curves obtained are similar to those obtained in buffer.

What is claimed is:

1. A method of determining blood levels of a pharmaceutical compound, at least a portion of which is complexed with an immunophilin to form a pharmaceutical-immunophilin complex, said method comprising:
   a. providing to a sample of the blood a binding competitor which displaces the pharmaceutical compound from the pharmaceutical-immunophilin complex by binding to the immunophilin in said sample,
   b. further providing to the blood sample a receptor which binds the pharmaceutical compound but is unable to significantly bind the binding competitor, whereby the pharmaceutical compound is released from the pharmaceutical-immunophilin complex to form a pharmaceutical-receptor complex capable of detection, and
   c. determining the amount of the pharmaceutical compound in said sample.

2. A method according to claim 1 wherein the pharmaceutical compound is Cyclosporin A.

3. A method according to claim 2 wherein the binding competitor is [Thr$^2$, Leu$^5$, D-Hiv$^8$, Leu$^{10}$]-Cyclosporin A.

4. A method according to claim 1 wherein the pharmaceutical compound is Cyclosporin A, the binding competitor is [Thr$^2$, Leu$^5$, D-Hiv$^8$, Leu$^{10}$]-Cyclosporin A, and the receptor is a monoclonal antibody.

5. A method according to claim 1 wherein the pharmaceutical compound is FK506; the binding competitor is Rapamycin; and the receptor is a monoclonal antibody.

6. A method according to claim 1 wherein the pharmaceutical compound is Rapamycin or 40-O-hydroxyethylrapamycin, the binding competitor is FK506, and the receptor is a monoclonal antibody.

7. An assay kit suitable for detecting the blood level of a pharmaceutical compound at least a portion of which is complexed with an immunophilin to form a pharmaceutical-immunophilin complex, said kit comprising a binding competitor capable of displacing the pharmaceutical from the pharmaceutical-immunophilin complex by binding to the immunophilin in said sample, and a receptor capable of binding the pharmaceutical to cause the pharmaceutical to be released from the pharmaceutical-immunophilin complex and to form a pharmaceutical-receptor complex capable of detection, said receptor being unable to significantly bind the binding competitor.

8. An assay kit according to claim 7 wherein the pharmaceutical compound is Cyclosporin A.

9. An assay kit according to claim 8 wherein the binding competitor is [$Thr^2$, $Leu^5$, $D-Hiv^8$, $Leu^{10}$]-Cyclosporin A.

10. An assay kit according to claim 7 wherein pharmaceutical compound is Cyclosporin A, the binding competitor is [$Thr^2$, $Leu^5$, $D-Hiv^8$, $Leu^{10}$]-Cyclosporin A, and the receptor is a monoclonal antibody.

11. An assay kit according to claim 7 wherein the pharmaceutical compound is FK506, the binding competitor is Rapamycin, and the receptor is a monoclonal antibody.

12. An assay kit according to claim 7 wherein the immunophilin-binding pharmaceutical is Rapamycin or 40-O-hydroxyethyl-Rapamycin, the binding competitor is FK506, and the receptor is a monoclonal antibody.

13. A method according to claim 1 wherein the pharmaceutical compound is FK506.

14. A method according to claim 13 wherein the binding competitor is Rapamycin.

15. A method according to claim 1 wherein the pharmaceutical compound is Rapamycin or 40-O-hydroxyethyl-rapamycin.

16. A method according to claim 15 wherein the binding competitor is FK506.

17. An assay kit according to claim 7 wherein the pharmaceutical compound is FK506.

18. An assay kit according to claim 17 wherein the binding competitor is Rapamycin.

19. An assay kit according to claim 7 wherein the pharmaceutical compound is Rapamycin or 40-O-hydroxyethyl-rapamycin.

20. An assay kit according to claim 19 wherein the binding competitor is FK506.

* * * * *